(12) United States Patent
Hall et al.

(10) Patent No.: US 6,886,392 B1
(45) Date of Patent: May 3, 2005

(54) SINGLE BALL BEARING LUBRICANT AND MATERIAL EVALUATOR

(75) Inventors: Philip B. Hall, Huntsville, AL (US); Howard L. Novak, Indialantic, FL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 10/622,174

(22) Filed: Jul. 17, 2003

(51) Int. Cl.⁷ .............................................. G01N 33/26
(52) U.S. Cl. ...................... 73/53.05; 73/53.06; 73/10
(58) Field of Search ........................... 73/53.05, 53.06, 73/10

(56) References Cited

U.S. PATENT DOCUMENTS

| | | | |
|---|---|---|---|
| 5,031,443 A | * | 7/1991 | Black et al. .................... 73/9 |
| 5,072,611 A | * | 12/1991 | Budd et al. ................. 73/118.1 |
| 5,275,258 A | | 1/1994 | Bousseau |
| 5,341,569 A | * | 8/1994 | Takamizawa et al. .... 29/898.09 |
| 5,509,198 A | * | 4/1996 | Takamizawa et al. .... 29/889.09 |
| 5,633,809 A | | 5/1997 | Wissenbach et al. |
| 5,959,189 A | | 9/1999 | Jeng et al. |
| 6,003,229 A | | 12/1999 | Beduhn et al. |
| 6,009,764 A | | 1/2000 | Fukunaga |
| 6,196,057 B1 | | 3/2001 | Discenzo |
| 6,324,899 B1 | | 12/2001 | Discenzo |
| 6,343,420 B1 | * | 2/2002 | Beduhn et al. ........... 29/898.07 |
| 6,378,382 B1 | * | 4/2002 | Noguchi et al. .......... 73/862.29 |
| 6,394,657 B1 | * | 5/2002 | Takamizawa et al. ........ 384/512 |
| 6,446,339 B2 | * | 9/2002 | Takamizawa et al. .... 29/898.09 |
| 6,712,518 B2 | * | 3/2004 | Takamizawa et al. ........ 384/450 |
| 2003/0101793 A1 | * | 6/2003 | Evans .............................. 73/9 |

* cited by examiner

Primary Examiner—Hezron Williams
Assistant Examiner—Rodney Frank
(74) Attorney, Agent, or Firm—James J. McGroary; Stephen J. Stark

(57) ABSTRACT

A test apparatus provides an applied load to a monoball through a trolley which moves along a loading axis. While applying the load to the monoball, the torque meter is in communication with the spherical monoball, and a load cell senses the application of applied force to the monoball. Meanwhile, a rotary actuary imports rotary oscillating motion to the monoball which is sensed by a position sensor and a torque meter. Accordingly, a processor can determine the coefficient of friction in substantially real time along with a cycles per second rate.

14 Claims, 2 Drawing Sheets

SINGLE BALL BEARING LUBRICANT AND MATERIAL EVALUATOR

ORIGIN OF THE INVENTION

This invention was made by an employee of the United States Government together with government support under contract awarded by the National Aeronautics and Space Administration and may be manufactured and used by or for the Government for governmental purposes without the payment of any royalties thereon or thereof.

BACKGROUND OF THE INVENTION

1. Field of the Invention

This invention relates to an apparatus for testing single ball bearings lubricants and/or materials in an oscillating rotary motion, and more particularly to such a test apparatus capable of providing environmental conditions including specific temperature, humidity, vacuum, atomic oxygen and other space simulated environmental conditions while monitoring the applied load, resisting torque, angle of rotation and/or coefficient of friction in real time.

2. Prior Art

A variety of lubricant and material test apparatuses have been produced. Falex Corporation maintains a web presence at www.falex.com and displays a number of test apparatuses they currently market and sell. None of these apparatuses are believed to test the performance of lubricants or materials relating to a single ball bearing subjected to oscillating rotary motion.

U.S. Pat. No. 6,324,899 shows a bearing sensor integration for a lubrication analysis system which allows various parameters of lubrication fluid to be sensed while the bearing is in use. The sensor integration described and shown in the '899 patent does not provide a testing apparatus for testing a monoball and the materials and/or lubricants utilized on a monoball in an oscillating early motion. Additionally, U.S. Pat. No. 6,196,057 shows an integrated multi-element lubrication sensor and lubricant health assessment which includes at least two sensors collecting data relating to a particular parameter of a fluid. This technology shown and described in this apparatus appears to be very similar to that taught in U.S. Pat. No. 6,324,899 also owned by Reliance Electric Technologies, LLC.

U.S. Pat. No. 6,009,764 shows a frequency discrimination type torque tester for use in determining bearing quality. This frequency discrimination type torque tester apparently breaks down a torque acting between an outer and an inner racing of a bearing into a spiky change component and an undulated change component. U.S. Pat. No. 6,003,229 shows an apparatus and method of precisely preloading a bearing onto a shaft. Neither of these devices are believed to be used as test apparatus for oscillatory rotary motion of spherical monoballs, lubricants and materials subjected to a measured applied loading and torque.

U.S. Pat. No. 5,959,189 shows a test apparatus of lubricating system with performance of rolling bearings. Specifically, the apparatus analyzes performance of a test bearing under different axial loads, rotating speed and lubrication conditions. This apparatus is not configured to evaluate spherical bearings under high loads, only roller type bearings and the condition of the lubricating system.

U.S. Pat. No. 5,633,809 shows a multi-function fluid flow monitoring apparatus with a velocity sensor capability. This device is a fluid phase monitoring apparatus which does not test bearings.

U.S. Pat. No. 5,275,258 shows an apparatus for detecting bearing-seize conditions in a reciprocating machine. This apparatus evaluates a condition of a liquid lubricant in a journal bearing and does not test solid film lubricants or greases in a slow oscillating motion under high loads.

U.S. Pat. No. 5,226,308 shows a system for testing bearings which utilizes a pair of spaced bearings and a bearing holder with an annular collar for holding the bearing to be tested. The bearing holder may be utilized to assist in applying a radial load to the bearing. This test apparatus is utilized with roller bearings under radial loads. It cannot be configured to test spherical bearings in a slow oscillating motion under high loads.

While numerous efforts have been made to test lubricants and materials with various bearings, there still exists a need to test a spherical bearing, lubricants and materials subjected to an oscillating rotary motion, particularly when under high load conditions in a controlled environment.

SUMMARY OF THE INVENTION

A need exists for an improved test apparatus for testing spherical ball bearings, lubricants and/or materials in oscillating rotary motion.

Another need exists for an improved oscillating rotary motion test apparatus for testing monoball bearings, lubricants, and/or materials under at least one of predetermined environmental conditions, torque conditions, oscillating rotation up to 280 degrees and/or cyclical rates from up to six cycles per second.

Another need exists for an oscillating rotary motion test apparatus capable of providing at least one environmental condition selected from a predetermined temperature, a predetermined humidity, a vacuum condition, an atomic oxygen concentration, and/or other simulated space environment.

Accordingly, a test apparatus applies a load to a monoball through a trolley which preferably configured to move only in the direction of the loading force. While applying a load to the monoball, oscillating rotary motion may be provided by a rotary actuator so that the monoball specimen, lubricant and/or material may be tested and sensed with sensors during testing. A load cell is useful to measure the applied load through the trolley to the specimen. The rotary actuary is equipped with a torque meter to measure resisting torque and a coupling may be utilized to account for misalignment, wear or compression of the monoball test specimen. A position sensor is connected to the shaft to measure angle of rotation of the shaft.

Finally, a data acquisition and control system is provided to receive data from the position sensor mounted on the shaft, the torque meter, and a compression load cell configured to measure the load imparted by the trolley on the monoball specimen so that a number of cycles and coefficient of friction may be calculated in real time and stored for post processing. Accordingly, control signals may be sent to the hydraulic cylinder and/or rotary actuator by the system.

BRIEF DESCRIPTION OF THE DRAWINGS

The particular features and advantages of the invention as well as other objects will become apparent from the following description taken in connection with the accompanying drawings in which.

DETAILED DESCRIPTION OF THE PREFERRED EMBODIMENT

Figure 1:
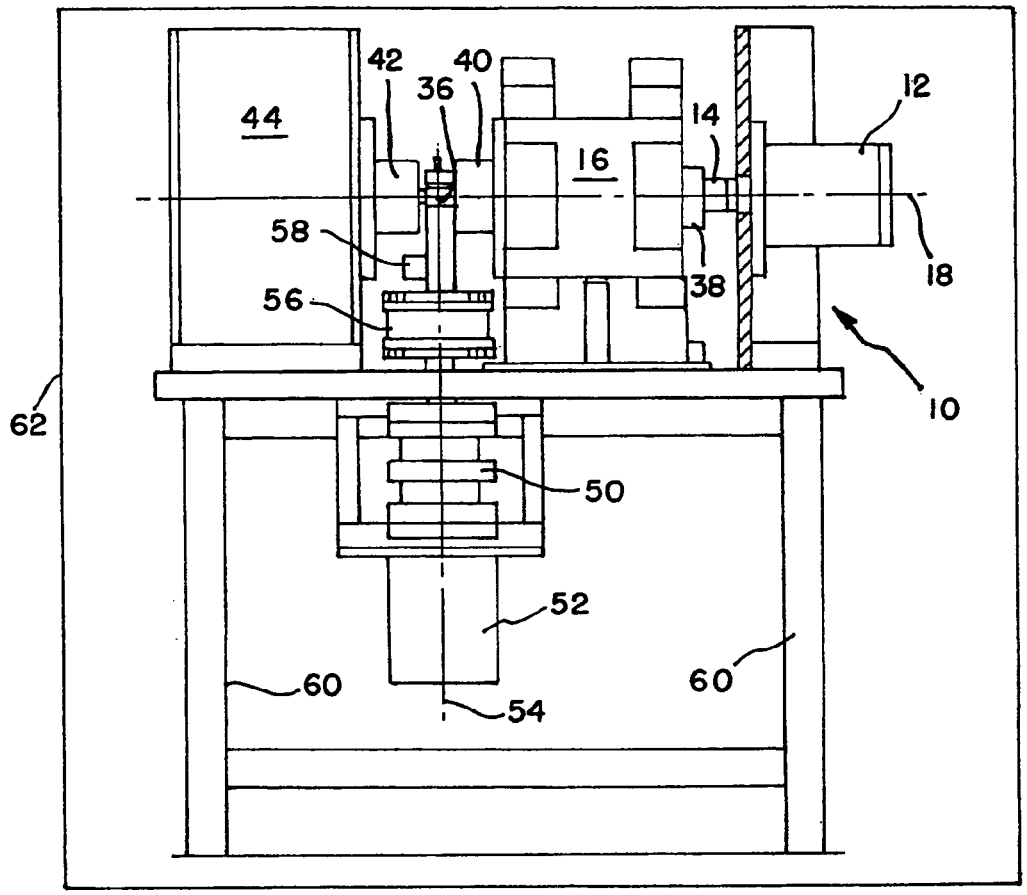
FIG. 1 is a side view of the test apparatus preferred by the present invention.
Figure 2:
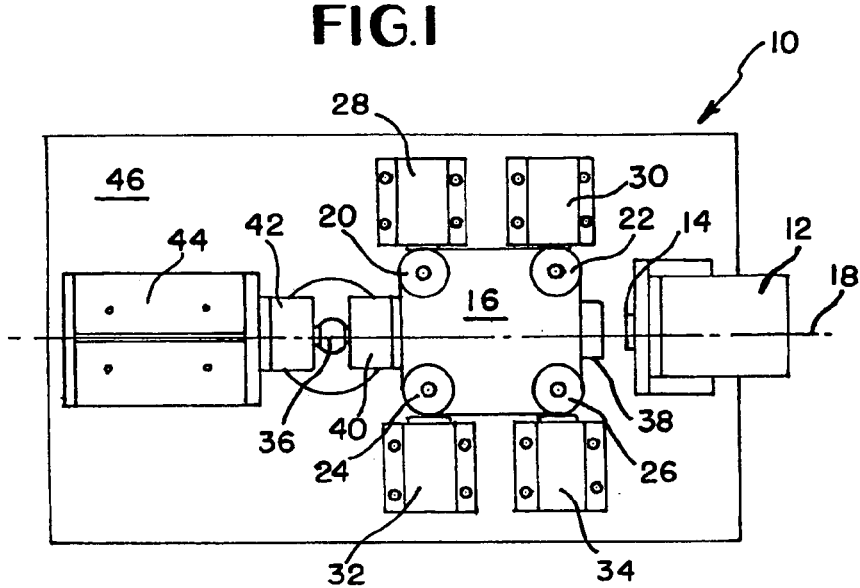
FIG. 2 is a top view of the test assembly shown in FIG. 1.

Accordingly, FIGS. 1 and 2 show a test apparatus 10 from a side and top view, respectively. The test apparatus 10 is comprised of a load applicator in the form of a hydraulic cylinder 12 which has an extendable piston 14 which contacts trolley 16. The hydraulic cylinder 12 of the load applicator is preferably configured to apply a load ranging from about 100 pounds to about 50,000 pounds of force or more. At the upper range of these loadings, the hydraulic cylinder 12 has been found to be a preferable load applicator. Other load applicators may be utilized in other embodiments.

The trolley 16 is preferably configured to travel along load axis 18. In fact, as shown in FIGS. 1 and 2, load axis 18 is linear and the trolley 16 is restricted to motion solely to travel along the load axis 18. Cam rollers 20,22,24,26 connected to trolley 16 are restrained from lateral motion by lateral supports 28,20,32,34. Accordingly, the trolley 16 is unable to travel in lateral motion by the lateral supports 28,30,32,34. However, the rollers 20,22,24,26 are moveable longitudinally, i.e., parallel to the load axis 18 so that the trolley 16 is moved toward and away from a specimen 36 with the extension and a withdrawal piston 14.

Once the piston 14 contacts load cell 38 and the contact face 40 contacts the specimen 36 up against receiver face 42, additional pressure from the hydraulic cylinder 12 applies a load which is measured by load cell 38. Depending on the amount of load applied, the load cell 38 records different loads applied through the trolley 16 on opposing sides of the contact face 40 and receiver face 42 which contact the specimen 36. Accordingly, a predetermined load may be applied and maintained by the hydraulic cylinder 12 through the trolley 16 to the faces 40,42 of opposing specimen 36. The contact face 40 and receiver face 42 for mating surfaces which oppose the specimen 36. The specimen 36 includes one or more monoball bearings (i.e., a single spherical bearing) and the applied lubricant and/or materials, if any.

Angle plate 44 is useful to support the receiver face 42 and provide a stable platform for receiving the force applied through the hydraulic cylinder 12 along the load axis 18. The angle plate 44 is preferably secured to table top 46 as illustrated in FIGS. 1 and 2. Additionally, the lateral supports 28,30,32,34 are also similarly secured to the tabletop 46. Finally the hydraulic cylinder 12 is also preferably secured to the table top 46. The trolley 16 is preferably restrained to travel along the load axis 18 but is not restrained to the table top 46. Additional cam rollers (obscured from view) are located below the trolley to support the weight of the trolley on the tabletop 46. These rollers which are obscured from view allow the trolley 16 to roll along the load axis while supporting the trolley 16 on the tabletop 46.

The test apparatus 10 is configured of test materials, lubricants and spherical bearings in oscillating rotary motion. In order to impart oscillating rotary motion to the bearing illustrated as specimen 36, the specimen 36 is connected to shaft 48 such as by being keyed onto the shaft 48 or otherwise connected to the shaft 48. The shaft 48 may be a Schmidt coupling 50 or be a series of connected shafts to allow for misalignment, wear and/or compression of the test specimen 36.

The Schmidt coupling 50 is also helpful to ensure equal loading on the contact face 40 and receiver face 42 relative to the specimen 36. Rotary actuator 52 imparts oscillating rotary motion about rotation axis 54 to specimen 36. It is preferable that the specimen 36 be rotatable through a range of oscillating rotation of up to 280 degrees in the preferred embodiment. Furthermore, the cyclical rate of rotation may vary intermediate anywhere from 0 to 6 cycles per second, depending upon the test to be run. A torque meter 56 is useful to measure resisting torque of the specimen 36 as it is oscillating under load applied by the hydraulic cylinder 12 through the trolley 16. Position sensor 58 is useful to sense the angle of rotation of the shaft 48 and thus the angle of rotation of the oscillating specimen 36.

The tabletop 46 is preferably supported by legs 60 so that the test apparatus 10 may be placed in a contained environment 62. The contained environment allows a predetermined temperature such as a temperature ranging from possible −320 degree Fahrenheit to 1000 degrees Fahrenheit to be applied during the testing conditions. Additionally, another environmental conditions, namely humidity, may be imposed in the environment 62 ranging from 0% to 100% relative. Additionally, the environment 62 may be made to be a vacuum such as a high vacuum or otherwise. The environment 62 may also be made to have a specific atomic oxygen content. Finally, the environment 62 may be made to simulate other space environmental conditions.

Figure 3:
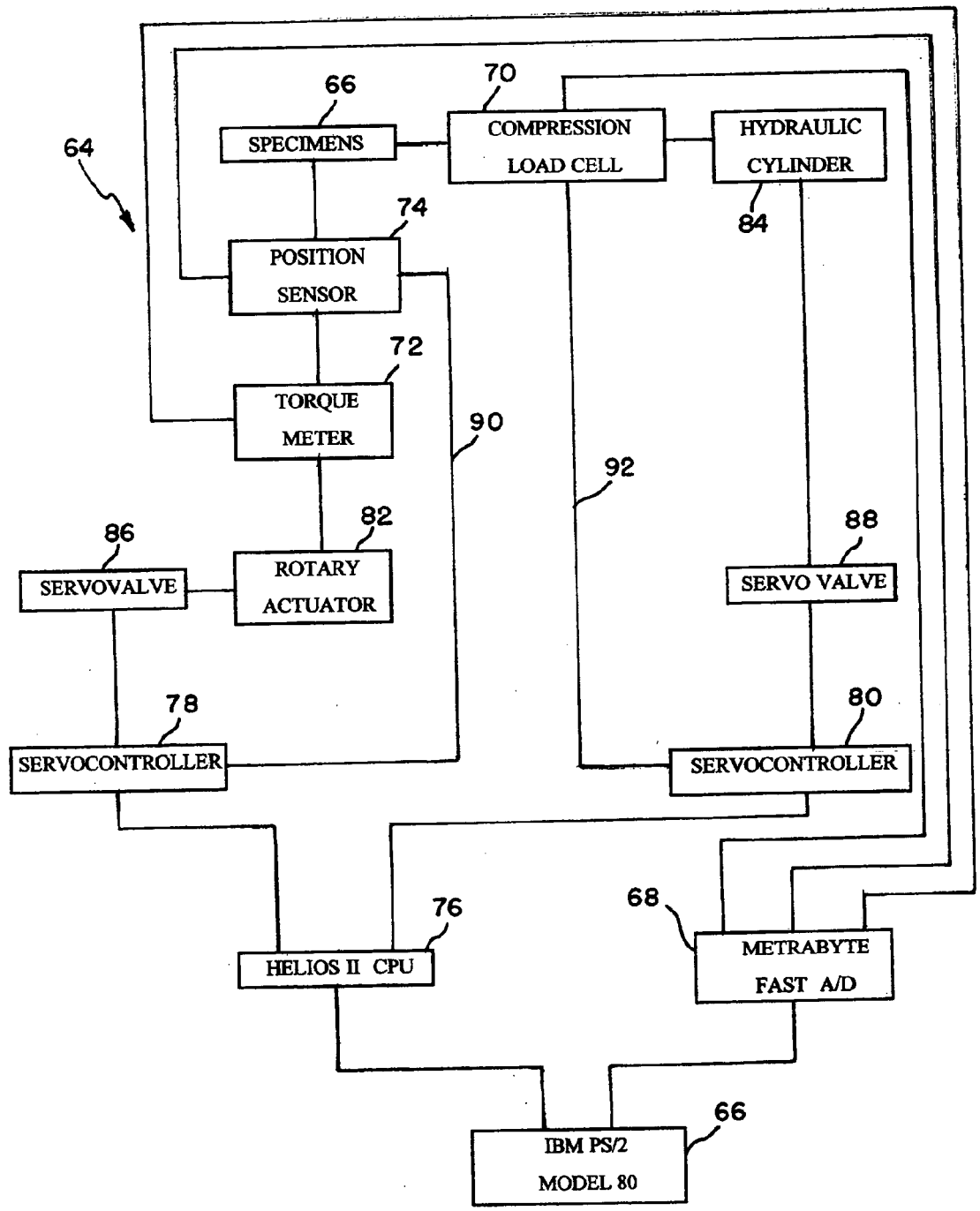
FIG. 3 is a schematic drawing of the data acquisition and control system utilized in conjunction with the test apparatus shown in FIGS. 1 and 2.

While FIGS. 1 and 2 show the mechanical structure of the test apparatus 10, FIG. 3 is useful to understand the data acquisition and control system 64. Of course, portions of the mechanical system shown in FIGS. 1 and 2 also comprised portions of the data acquisition control system 64. After locating the test specimen or specimens 36 on the shaft 48 as shown in Figure, particular lubricants and/or materials such as the material of the bearing or other materials may be applied to the contact face 40, or receiver face 42, or to the bearing directly. Accordingly, these lubricants, materials or bearings which form the specimen 36 may be tested by the test apparatus 10. The heart of the data acquisition and control system 64 is a processor 66 illustrated as an IBM PS2 Model 80. However, many other suitable processors such as a PC Lap Notebook, a desktop computer or even a portable data assistant (PDA) could be utilized. The processor 66 receives an input from one or more analog to digital (A/D) converters 68 which receives inputs from the compression load cell block 70, the torque meter block 72 and the position sensor block 74. The load cell block 70 receives data from the load cell 38 shown in FIGS. 1 and 2. The position sensor block 74 receives data from the position sensor 58 and the torque meter block 72 receives data from the torque meter 56 appropriately. The physical connectors from the position sensor 58, the torque meter 56 and the load cell 38 are not illustrated but are known to those skilled in the art.

The data received from the analog digital converter 68 is converted to digital and provided to the processor 66 for processing. The analog to digital converter 68 is preferably a Metrabyte (™) or equivalent fast analog to digital (A/D) input controller card or other appropriate analog to digital controller device. Based upon the data received from the torque meter block 72, position sensor block 74 and compression load cell block 70, the processor 66 can calculate the number of cycles and the coefficient of friction substantially in real time. The data may also be stored in the processor 66 for post-processing. In the preferred embodiment, the operator does not need to perform any task once the test apparatus has been started.

In order to perform processes, the processor 66 provides command signals preferably to a controller 76 such as a Fluke Helios II, an equivalent micro processor, or other appropriate controller. Of course, the processor 66 and controller 76 may be the same unit in some embodiments. Instructions and/or commands are then provided from the controller 76 to servo controllers 78,80 which effectively control the rotary actuator 82 and hydraulic cylinder 84 through servo valves 86 and 88 respectively. Feedback loops 90,92 are useful to provide input from the position sensor block 74 back to the servo controller 78 for the rotary actuator 82 and as well as from the compression load cell 70 to the servo controller 80 for controlling the hydraulic cylinder 84. Accordingly, the processor 66 and/or controller 76 can provide the necessary commands to specify the loads provided or imposed upon the specimen 36 by the hydraulic cylinder 84 through the load cell 38 as well as the action of the rotary actuator 52 to provide a desired oscillating rotary position as sensed by the position sensor 74 on the specimens 66 so that the applied torque may be measured by the torque meter 72.

The servo controllers 78,80 are particularly useful in controlling servo valves of hydraulic systems so that the rotary actuator and hydraulic cylinders 82,84 may be hydraulically operated. The hydraulic servo valve 86,88 vary the hydraulic pressure and/or flow to the hydraulic cylinder 84 and rotary actuator 82 respectively. Return data may be provided to the processor 66 from the controller 76 depending upon the capabilities of the particular controller 76 selected. If hydraulics are not utilized, the servo controllers 78,80 and servo valves 86,88 maybe replaced with appropriate devices to control the applied load and position of the specimen 36.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. A test apparatus comprising:
  a trolley restricted from movement in a lateral direction by lateral restraints;
  a load applicator in communication with the trolley configured impart a load through the trolley along a load axis, said load axis perpendicular to the lateral direction;
  mating surfaces comprised of a contact face and a receiving face, said contact face connected to the trolley;
  a spherical bearing intermediate the contact face and the receiving face;
  a rotary actuator coupled to the spherical bearing imparting oscillating rotary motion to the spherical bearing upon command along a rotation axis;
  a load sensor configured to sense a load along the load axis;
  a torque sensor configured to sense a torque along the rotation axis; and
  a processor in communication with the load sensor and torque sensor, said processor providing a coefficient of friction substantially in real time.

2. The test apparatus of claim 1 further comprising a position sensor configured to sense a relative position of the spherical bearing as it is rotated about the rotation axis by the rotary actuator.

3. The test apparatus of claim 1 wherein the position sensor is in communication with the processor and the processor calculates a cycles per second value for the oscillating rotation of the spherical bearing.

4. The test apparatus of claim 1 further comprising one of a lubricant and a material applied to one of the spherical bearing, the contact face and the receiving face.

5. The test apparatus of claim 1 further comprising a controlled environment providing one of a temperature intermediate about −320 F. to about a 1,000 F., a humidity intermediate 0 to 100%, a predetermined vacuum, and a predetermined atomic oxygen content, said controlled environment provided at least about the spherical bearing.

6. The test apparatus of claim 1 wherein the rotary actuator is coupled with a Schmidt type coupler to the spherical bearing.

7. The test apparatus of claim 1 wherein the spherical bearing is fixedly connected to a shaft coupled to the rotary actuator.

8. The test apparatus of claim 1 wherein the rotary actuator is hydraulically actuated and controlled by a servo motor in communication with a servo controller, and
  said servo controller receives a signal from a controller.

9. The test apparatus of claim 8 wherein the controller is in communication with the processor.

10. The test apparatus of claim 8 wherein the controller is a Fluke Helios II.

11. The test apparatus of claim 8 wherein the controller is also in communication with a servo controller which provides a signal to a servo motor in hydraulic fluid communication with the load applicator.

12. The test apparatus of claim 11 wherein the load applicator is hydraulically operated and comprises a hydraulic cylinder which extends a piston which is communicates an applied load through the trolley to the spherical bearing.

13. The test apparatus of claim 1 wherein the processor provides the command to rotate the spherical bearing in rotary oscillating motion.

14. The test apparatus of claim 1 wherein the processor also provides commands to apply load through the load applicator to the spherical bearing.

* * * * *